United States Patent
Thompson et al.

[11] Patent Number: 5,860,993
[45] Date of Patent: Jan. 19, 1999

[54] SUTURE CUTTER

[75] Inventors: Ronald J. Thompson, Ft. Thomas, Ky.; William Mers Kelly, Xenia, Ohio

[73] Assignee: Medworks Corp., Louisville, Ky.

[21] Appl. No.: 719,487

[22] Filed: Sep. 25, 1996

[51] Int. Cl.[6] .................................................. A61B 17/04
[52] U.S. Cl. ........................... 606/148; 606/172; 30/151
[58] Field of Search .................................. 606/167, 170, 606/172; 30/151, 162

[56] References Cited

U.S. PATENT DOCUMENTS

| | | |
|---|---|---|
| 719,799 | 2/1903 | Hill ............................................ 30/241 |
| 2,541,063 | 2/1951 | Hubbard ..................................... 30/241 |
| 3,590,808 | 7/1971 | Muller . |
| 3,802,074 | 4/1974 | Hoppe . |
| 3,995,619 | 12/1976 | Glatzer . |
| 4,799,483 | 1/1989 | Kraff . |
| 5,037,433 | 8/1991 | Wilk et al. . |
| 5,053,043 | 10/1991 | Gottesman et al. . |
| 5,087,263 | 2/1992 | Li . |
| 5,129,912 | 7/1992 | Noda et al. . |
| 5,133,723 | 7/1992 | Li et al. ................................... 606/148 |
| 5,152,744 | 10/1992 | Krause et al. . |
| 5,163,946 | 11/1992 | Li . |
| 5,211,650 | 5/1993 | Noda ....................................... 606/139 |
| 5,250,055 | 10/1993 | Moore et al. . |
| 5,282,807 | 2/1994 | Knoepfler . |
| 5,282,809 | 2/1994 | Kammerer et al. . |
| 5,314,433 | 5/1994 | Li . |
| 5,336,229 | 8/1994 | Noda ....................................... 606/140 |
| 5,336,231 | 8/1994 | Adair . |
| 5,364,410 | 11/1994 | Failla et al. . |
| 5,387,221 | 2/1995 | Bisgaard . |
| 5,395,391 | 3/1995 | Essig et al. . |
| 5,423,837 | 6/1995 | Mericle et al. . |
| 5,423,844 | 6/1995 | Miller ...................................... 606/171 |
| 5,439,467 | 8/1995 | Benderev et al. . |
| 5,439,470 | 8/1995 | Li . |
| 5,452,513 | 9/1995 | Zinnbauer et al. ........................ 30/140 |
| 5,545,170 | 8/1996 | Hart . |
| 5,549,618 | 8/1996 | Fleenor et al. ........................... 606/170 |
| 5,562,693 | 10/1996 | Devlin et al. ............................ 606/174 |

FOREIGN PATENT DOCUMENTS

| | | |
|---|---|---|
| 0440991 | 8/1991 | European Pat. Off. . |
| 0669103 | 8/1995 | European Pat. Off. . |
| 1225547 | 8/1984 | United Kingdom . |

*Primary Examiner*—Gary Jackson
*Attorney, Agent, or Firm*—Dinsmore & Shohl LLP

[57] ABSTRACT

An apparatus for cutting a suture is provided. The apparatus comprises a housing having at least one groove therein; and a knife moveable between retracted and extended positions, and positioned within the housing such that the knife passes through the groove as it is moved from the retracted position to the extended position, thereby cutting a suture positioned within the groove. A suture retainer for preventing a suture from escaping the groove prior to the cutting step is also provided. A method of cutting a pair of suture tails extending from a knot is also provided.

32 Claims, 6 Drawing Sheets

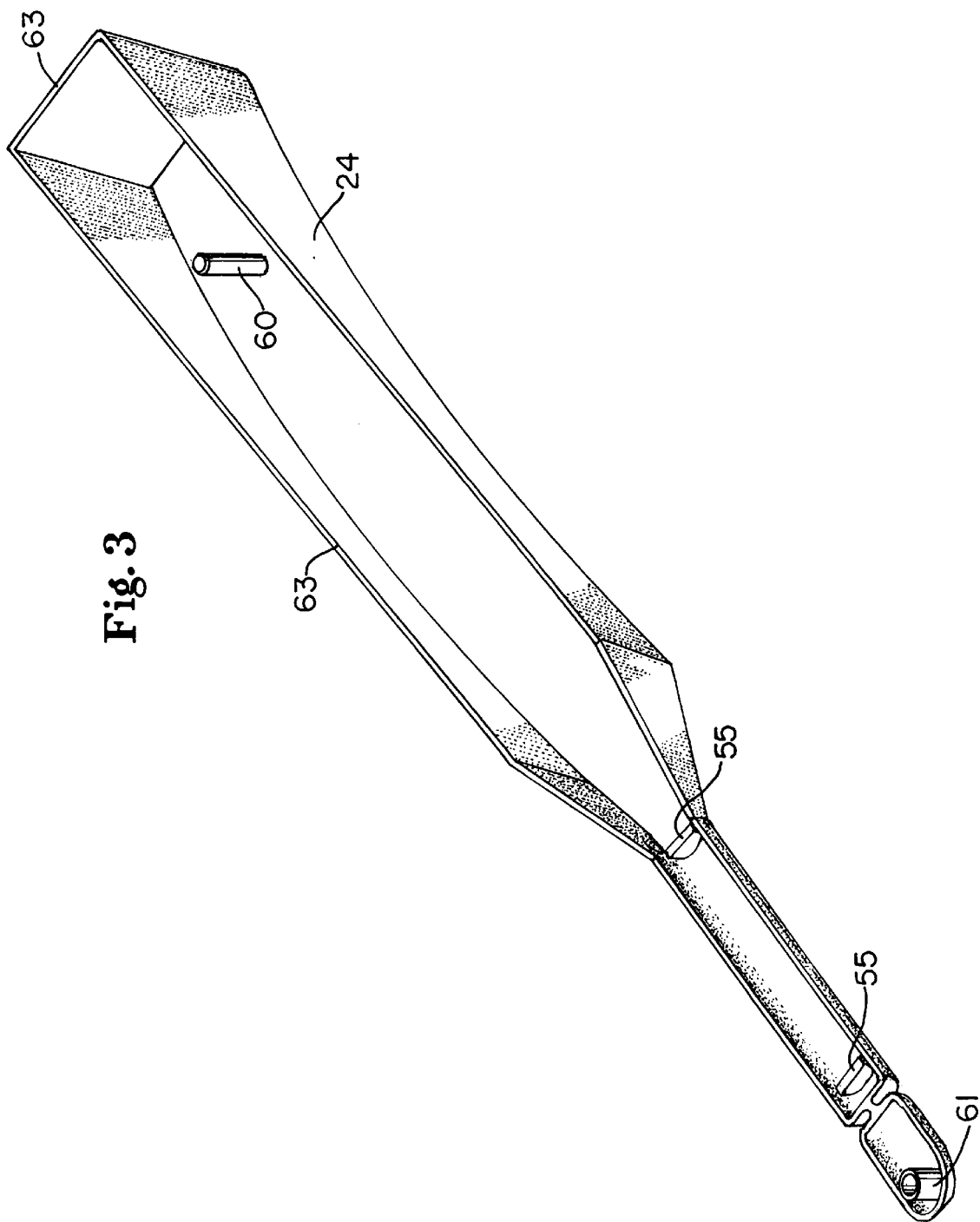

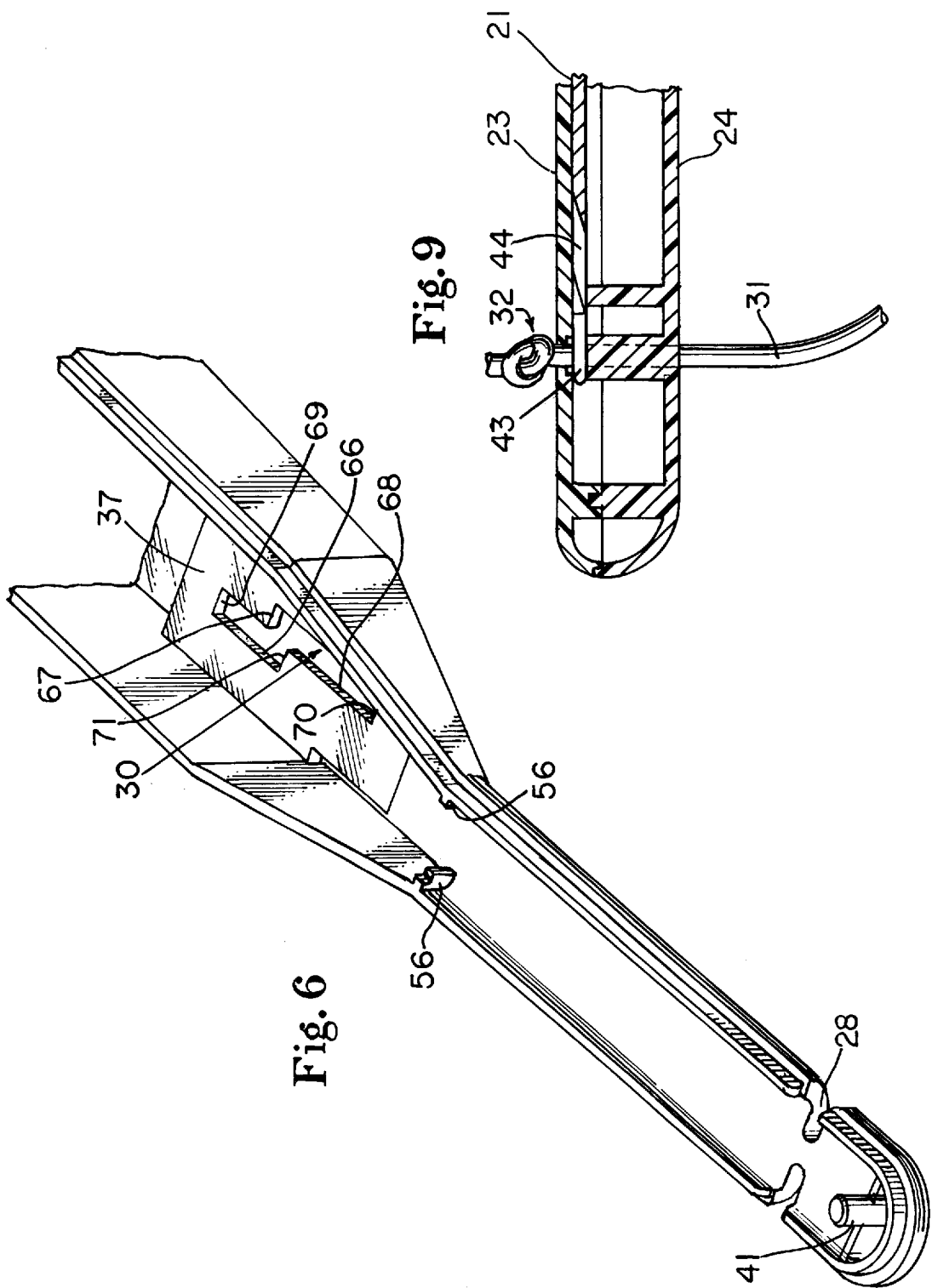

SUTURE CUTTER

BACKGROUND OF THE INVENTION

1. Field of the Invention

This invention relates to a suture cutter, as well as a method of cutting a pair of suture tails using this suture cutter. More particularly, the present invention provides a suture cutter which may be employed to safely cut one or more suture tails which are positioned at a location which is not easily accessible to traditional suture cutting means.

2. Description of Related Art

The majority of surgical procedures rely upon various types of sutures for not only closing incisions, but also for connecting and/or supporting structures within the body. The use of sutures also usually requires the tying of one or more knots in order to secure the suture in place. After these knots are tied, the pair of suture tails extending from the knot normally must be cut. If the tails are cut too short or unevenly, the knot may become untied. Alternatively, if the tails are left too long, the suture tails may be irritating to the patient or become entangled with other structures.

The cutting of suture tails can often be accomplished merely by employing surgical scissors, particularly when the knot is located outside of the patient's body. Many times, however, the knot and accompanying suture tails are located within the patient's body, or within an orifice of the patient's body. For example, sutures may be tied within the abdomen of a patient during a surgical procedure. In these instances, it may be difficult for medical personnel to safely employ standard surgical scissors to cut the sutures after tying. Thus, various types of suture-cutting devices have been developed which enable the medical personnel to cut the sutures in a location which normally would not be accessible to a pair of conventional scissors. These devices of the prior art suffer from many drawbacks, however, including the risk of the cutting blade inadvertently injuring the patient or physician. In addition, vision is often impaired during these procedures, and thus it can be difficult for the medical personnel to insure that the suture tails are left at the proper length. Most of these devices are also unable to simultaneously cut both tails.

One particular surgical procedure where cutting suture tails can be problematic is laparoscopic urethropexy for treating stress urinary incontinence in women. This procedure is described in U.S. patent application Ser. No. 08/519,606, which is herein incorporated by reference. In this procedure, one or more bone anchors are laparoscopically secured to the pubic bone of the patient, preferably adjacent to the space of Retzius. A suture extends from each anchor, and is preferably looped through an aperture in the anchor such that a pair of suture tails extend from the anchor. The suture tails are then pulled into the vagina, preferably by a suture-retrieving device which passes through the vaginal mucosa and enters the abdominal cavity to grasp the suture tails. The suture tails are brought through the entire thickness of the periurethral fascia and vaginal mucosa such that each tail penetrates the tissue at a predetermined distance from the other tail, and from the urethra. These tails may then be tied to one another in order to elevate the urethra and thereby eliminate the incontinence.

Once the suture tails are tied to one another within the vagina, the tails must be cut. If the tails are cut too close to the knot or unevenly, the knot is likely to become untied, thereby eliminating the correction provided by the surgery. If the tails are left too long, on the other hand, the excess suture material will cause irritation to the patient and may not be fully epithelialized. Properly cutting the suture tails within the vagina can be difficult, however, due not only to the confined space, but also due to the lack of operative vision. Surgical scissors and the like may not only cut the tails at an improper or uneven length, but may also damage vaginal tissue during the process. It is also difficult to simultaneously cut more than one suture tail with conventional scissors.

The present invention offers a unique suture cutter designed to easily cut sutures located within a body cavity or orifice. This suture cutter is particularly suited for simultaneously cutting suture tails to their proper length during the above-described laparoscopic urethropexy procedure.

SUMMARY OF THE INVENTION

It is an object of the present invention to provide a suture cutting apparatus.

It is another object of the present invention to provide a suture cutter wherein the knife for cutting the suture is not exposed.

It is yet another object of the present invention to provide a suture cutter wherein a pair of suture tails extending from a knot may be cut a predetermined and equivalent distance from the knot.

It is still another object of the present invention to provide a suture cutter which may be employed to safely cut suture tails located in a body orifice or otherwise hidden from the view of medical personnel.

The foregoing objects can be accomplished by providing, in accordance with one embodiment of the present invention, an apparatus for cutting a suture comprising:

(a) a housing having a groove therein; and (b) a knife moveable between retracted and extended positions, and positioned within the housing such that the knife passes through the groove as it is moved from the retracted position to the extended position, thereby cutting a suture positioned within the groove.

The suture cutter further comprises a suture retainer moveable between open and closed positions, wherein the retainer permits a suture to be positioned within the groove when the retainer is at its open position, and the retainer prevents a suture from escaping from the groove when the retainer is at its closed position.

The suture retainer and knife are preferably provided at the distal end of a moveable shank positioned within the housing, and this shank is moveable between retracted, intermediate and extended positions. When the shank is at its retracted position, the knife is at its retracted position and the retainer is at its open position. When the shank is at its intermediate position, the retainer is at its closed position. Finally, when the shank is at its extended position, the knife is at its extended position. An actuator for effecting movement of the shank is also preferably provided, and is disposed on the surface of the housing for easy accessibility. The housing preferably has a handle portion and an elongate neck portion, wherein the actuator is located on the handle and the groove is located on the neck.

The suture retainer preferably comprises a prong at the distal end of the shank. Since the groove has an entrance through which the suture enters the groove, the prong is configured so as to block the entrance to the groove when the shank is at its intermediate position. By blocking the entrance to the groove, a suture is prevented from escaping from the groove while still permitting the suture to slide within the groove. The knife is preferably located on the shank proximally of the prong such that the knife will only enter the groove to cut a suture as the shank is moved from its intermediate position to its extended position.

When the suture cutter is to be employed to cut a pair of suture tails extending from a knot, it is preferred that a pair of grooves be provided on either side of the housing neck. A pair of suture retainers are also preferably provided in order to retain a suture tail in each of the grooves. Each of the suture retainers, however, still preferably comprises a prong extending from the distal end of the shank, and the knife is located proximally of both prongs. More preferably, the knife comprises a pair of cutting edges such that when the shank is moved to its extended position, one of the cutting edges passes through each of the grooves. These cutting edges may be arranged in a V-shaped configuration, and the prongs and cutting edges may also define a similar shape. In order to provide more control to the movement of the shank, the actuator is preferably moveable in a substantially Z-shaped pattern corresponding to the retracted, intermediate and extended positions of the shank. A Z-shaped or stepped slot may be provided in the housing in order to guide the actuator in this pattern.

A method for cutting a pair of suture tails extending from a knot employing the above-described suture cutter is also provided. This method comprises the steps of:

(a) providing a suture cutter comprising:
 a housing having a pair of grooves therein; and
 a knife moveable between retracted and extended positions, and positioned within the housing such that the knife will cut a suture tail positioned within each of the grooves as the knife is moved to its extended position;

(b) positioning one of the tails in each of the grooves while the knife is at its retracted position; and (c) moving the knife to its extended position, thereby cutting the suture tails adjacent the knot.

This method may further comprise the step of sliding the suture cutter along the suture tails to the knot prior to cutting the tails, thereby cutting the tails at a predetermined distance from the knot.

BRIEF DESCRIPTION OF THE DRAWINGS

While the specification concludes with claims particularly pointing out and distinctly claiming the present invention, it is believed the same will be better understood from the following description taken in conjunction with the accompanying drawings in which:

FIG. 3 is a perspective view of the bottom half of the housing of the suture cutter of FIG. 1;

FIG. 6 is a perspective view of a portion of the top half of the housing of the suture cutter of FIG. 1;

FIG. 9 is cross-sectional view of the neck portion of the suture cutter of FIG. 1, taken along the line 9—9 thereof, along with a suture tail about to be cut adjacent a knot.

DESCRIPTION OF THE PREFERRED EMBODIMENTS

Figure 1:
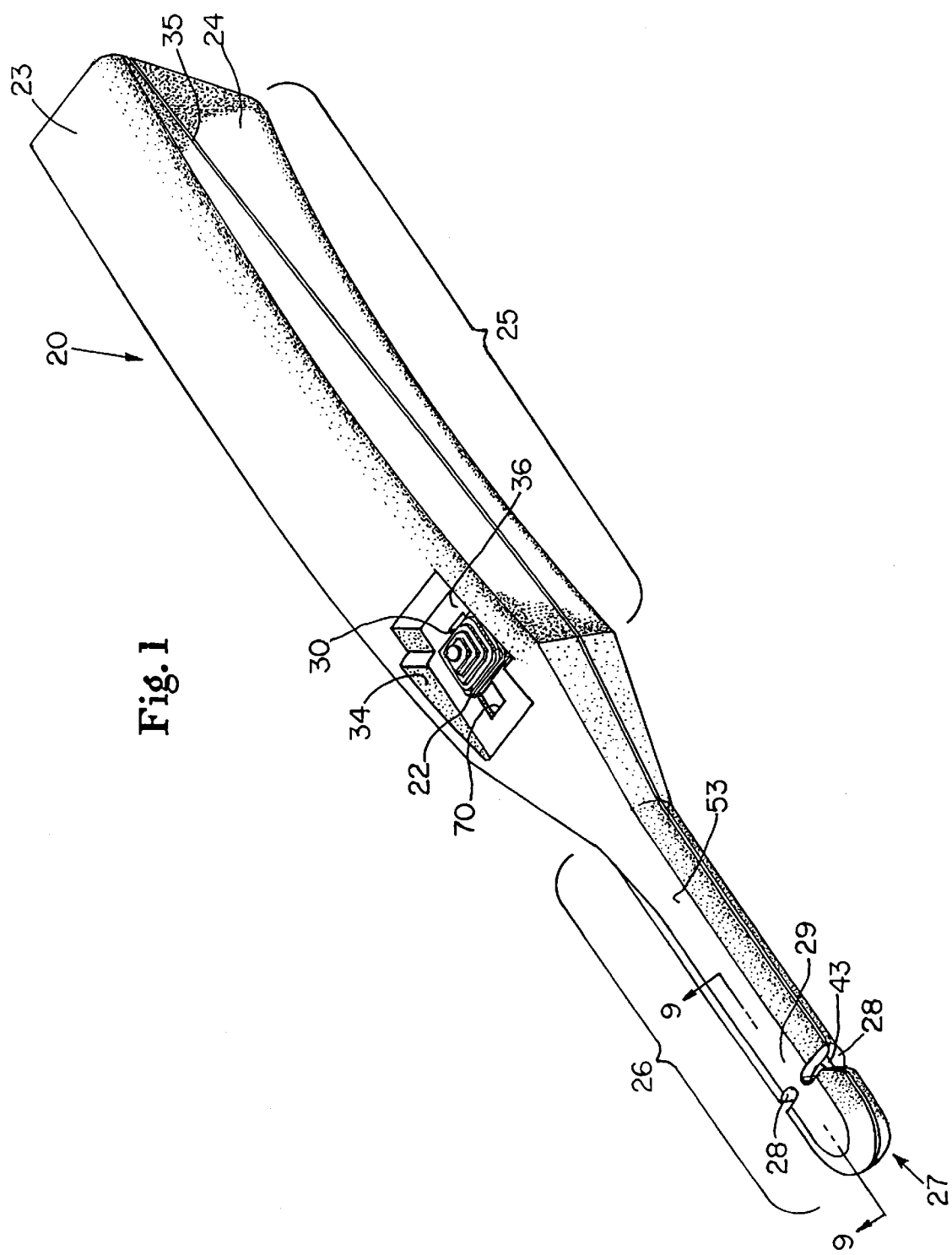
FIG. 1 is a perspective view of the suture cutter of the present invention.
Figure 2:
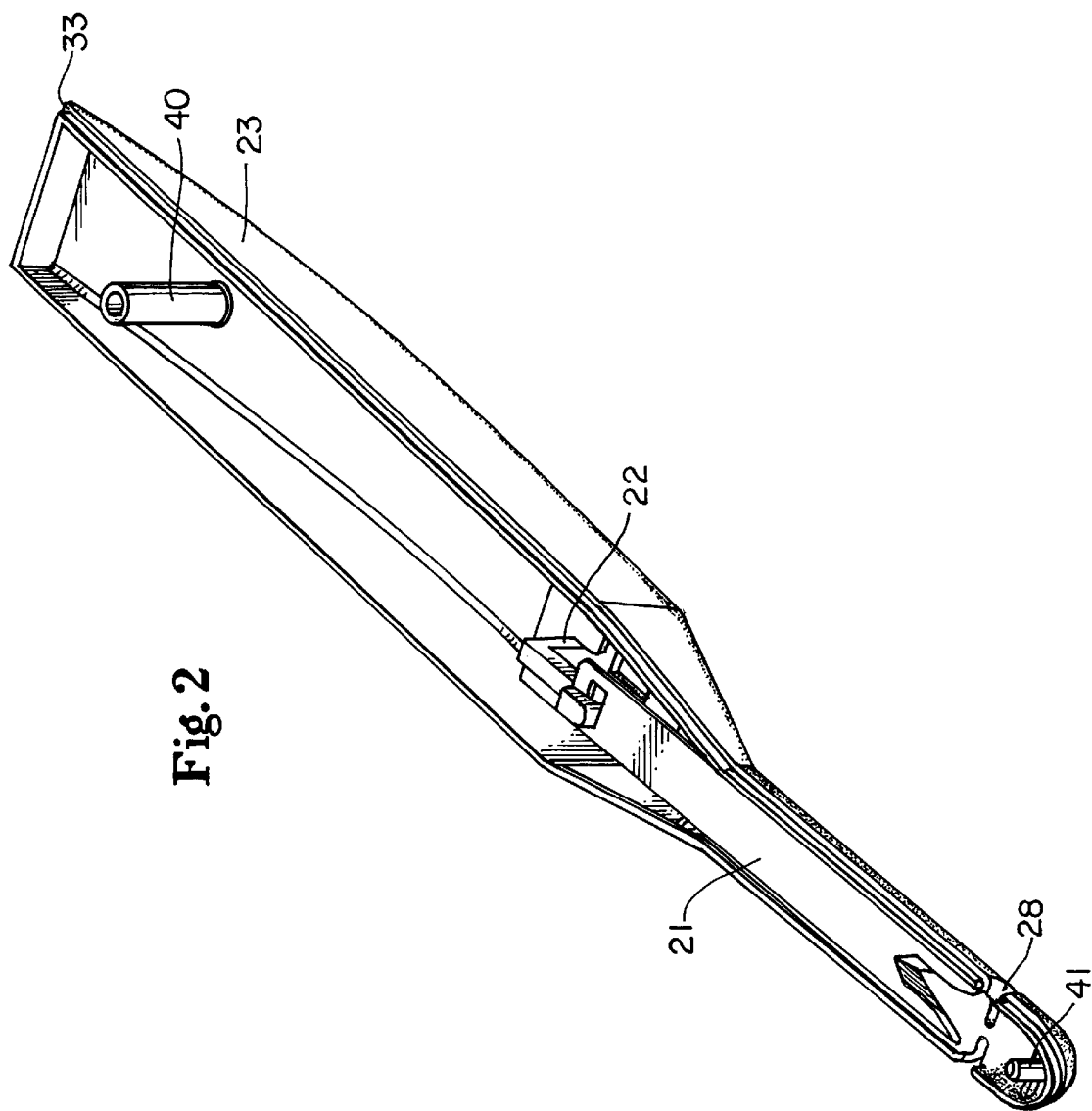
FIG. 2 is a perspective view of the top half of the housing of the suture cutter of FIG. 1 along with the moveable shank and a portion of the actuator, wherein the shank is at its retracted position.

FIG. 1 is a perspective view of a suture cutter according to one embodiment of the present invention. The suture cutter comprises a housing 20 which is formed from top-half 23 and bottom-half 24. Housing 20 may be made from any of a number of materials, however, lightweight, molded plastic is preferred both for its cost and ease of manufacture. Top-half 23 (which is depicted in FIG. 2) and bottom-half 24 (which is depicted in FIG. 3) have corresponding peripheral edges which may be joined to one another at seam 35 as shown in FIG. 1 and as known to those skilled in the art. To facilitate the alignment of top-half 23 and bottom-half 24, a shoulder 33 preferably extends about the periphery of top-half 23 as best shown in FIG. 2. The corresponding peripheral edge 63 of bottom-half 24 (FIG. 3) will matingly engage shoulder 33 in order to facilitate alignment of top-half 23 and bottom-half 24. Top-half 23 and bottom-half 24 may then be secured to one another along seam 35 by conventional means well-known in the art, such as an adhesive. The mating engagement of the top and bottom halves also assists in preventing fluids and the like from entering housing 20 during use.

Housing 20 is preferably of a hollow construction, not only to save on cost and weight, but also to allow movement of a shank which is described further herein. Therefore, in order to not only assist in aligning top-half 23 and bottom-half 24, but also to add rigidity to housing 20, internal support structures may also be provided. Thus, first upright cavity 40 and peg 41 are provided in top-half 23. Corresponding first peg 60 and second upright cavity 61 are likewise provided in bottom half 24. When the two halves of housing 20 are joined to one another, each peg will be secured within its corresponding upright cavity, thereby providing additional support to housing 20. Preferably, each peg and its corresponding upright cavity are of hexagonal or circular cross-section.

Housing 20 preferably comprises a handle portion 25 and a neck portion 26. Handle 25 is preferably configured so as to be easily grasped and manipulated by medical personnel during use. Handle 25 tapers in size to neck 26 which is preferably of a smaller cross-sectional area than handle 25. As described more fully below, the top surface 53 of neck 26 is preferably flat, while the remainder of neck 26 is of a rounded or arcuate cross-section. As will be more fully understood herein, neck 26 may be of any suitable length, and its length will primarily depend upon the intended use for the suture cutter of the present invention. For example, the suture cutter of the present invention may be employed vaginally during a laparoscopic urethropexy procedure, and thus neck 26 should be sized accordingly. Alternatively, the suture cutter of the present invention may even be employed laparoscopically through a trocar, and thus neck 26 may be lengthened considerably for such use. Neck 26 terminates in tip 27, which is preferably smooth and rounded in order to prevent patient injury.

Disposed along the length of neck 26 are one or more grooves 28. These grooves 28 are sized to accommodate a suture, and as will be more fully understood below, provide an isolated region wherein the sutures may be cut. Since the cutting edge of the knife will pass through these grooves, a suture to be cut may conveniently be placed within these grooves for cutting. In this manner, the use of grooves 28 will prevent inadvertent injury caused by the cutting edge of the knife. It should be noted that the term "suture tail" is meant to include any length of suture, whether or not it is extending from a knot.

In the preferred embodiment of FIG. 1, a pair of grooves 28 are provided on opposite sides of neck 26 in the manner shown. To facilitate insertion of the suture tails into grooves 28, the width of the grooves preferably tapers inwardly such that the grooves are their widest at the side surfaces of neck 26. The space 29 between the pair of grooves and the embodiment of FIG. 1 is selected so that the suture tails will be cut a predetermined and proper dist knot. As shown in FIG. 9 which depicts a suture tail positioned within groove 28 and about to be cut by the internal knife further described herein, knot 32 may rest upon space 29. Thus, as space 29 is widened, suture tail 31 will be cut at a greater distance from knot 32. In addition, by flattening top surface 53 of neck 26, the suture tail will be cut closer to knot 32.

Depending upon the intended use of the suture cutter of the present invention, any of a number of grooves 28 may be provided along the length of neck 26. Thus, even a single groove 28 may be provided. In addition, a plurality of grooves may be positioned along the same side of neck 26. Thus, the present invention is not limited to a suture cutter having a pair of grooves on opposite sides of neck 26. As will be more fully understood below, the shape and configuration of shank 21 (FIG. 4) will depend upon the number and location of grooves 28.

Figure 4:
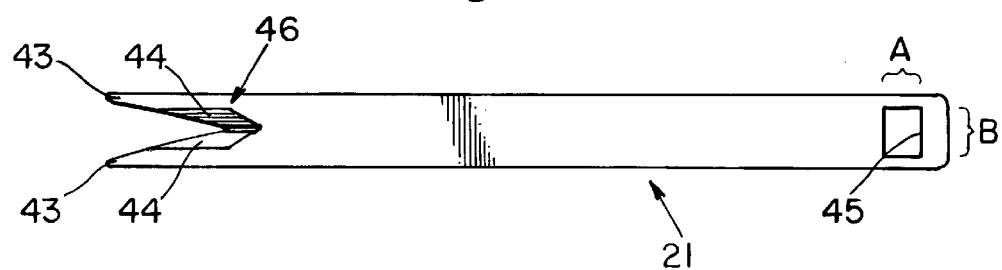
FIG. 4 is a top plan view of the shank of the suture cutter of the present invention.

Shank 21 is depicted in FIG. 4 and comprises a elongate member preferably made of metal (particularly stainless steel). Shank 21 has a slot 45 at its proximal end, and a pair of suture retainers are positioned at its distal end. The suture retainers preferably comprise a pair of prongs 43 extending from the distal end of shank 21. Preferably, prongs 43 are at their narrowest at the distal end of shank 21, and taper towards knife 46. Knife 46 may comprise any suitably shaped cutting edge, however it is preferred that a pair of cutting edges 44 are provided. Cutting edges 44 are configured in a V-shaped arrangement, and meet along the centerline of shank 21. Thus, the pair of prongs 43 and cutting edges 44 form a substantially V-shaped region at the distal end of knife 21. Alternatively, knife 46 may comprise a single cutting edge provided in a straight or even curved configuration. In addition, while cutting edges 44 should be sufficiently sharp to easily cut sutures, the interior edge of prongs 43 should be smooth and generally incapable of cutting sutures.

Shank 21 is slidably disposed within the interior of housing 20 as best shown in FIG. 2. It is preferred that the movement or sliding of shank 21 occur only along a line parallel to the longitudinal access of housing 20. Thus, the width of shank 42 is preferably slightly smaller than the interior width of neck 26, which thereby prevents shank 21 from moving laterally. A pair of shank supports 55 are provided along the interior of neck portion 26 on bottom half 24 of housing 20. As best shown in FIG. 3 which depicts the interior of bottom half 24 of housing 20, shank supports 55 provide a flat surface upon which shank 21 may slide. Corresponding shank guides 56 are also preferably provided in top half 23 of the housing as shown in FIG. 6, and these shank guides assist in aligning the shank particularly during assembly. Both shank supports 55 and shank guides 56 may be integrally molded into bottom half 24 and top half 23.

Figure 7:
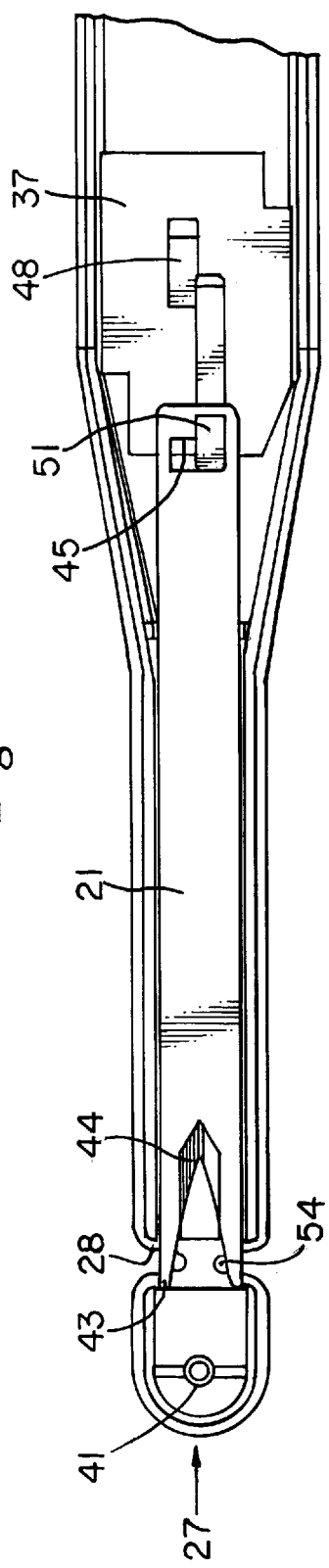
FIG. 7 is a top plan view of a portion of the top half of the housing of the suture cutter of FIG. 1, wherein the shank is at its intermediate position.
Figure 8:
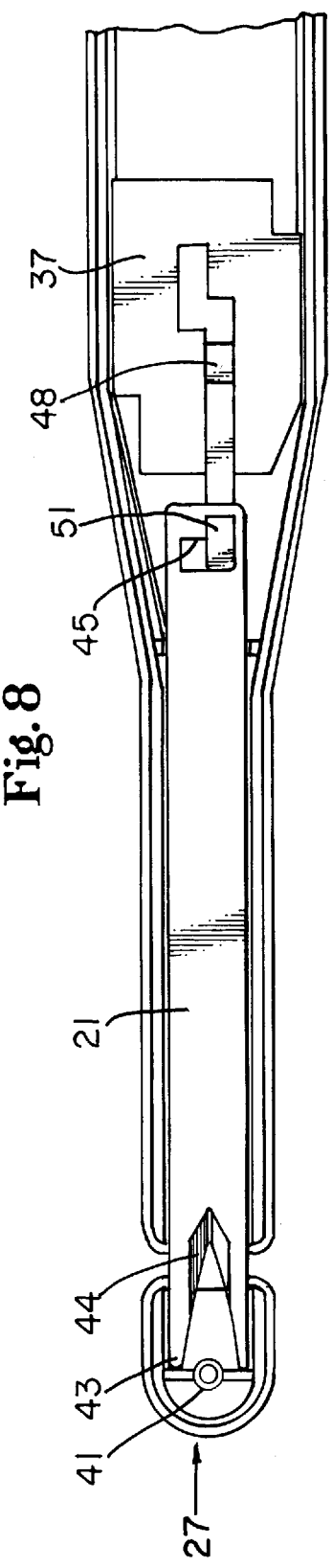
FIG. 8 is a top plan view of a portion of the top half of the housing of the suture cutter of FIG. 1, wherein the shank is at its extended position.

Movement of shank 21 is best shown in FIGS. 2, 7 and 8. Shank 21 is moveable between a retracted position, a suture-holding (or intermediate) position and a suture-cutting (or extended) position. When the shank is in its retracted position, the suture retainers (prongs 43) are in their open position (i.e., not present in the grooves), thereby permitting suture tails to be inserted into grooves 28. In FIG. 2, shank 21 is in its retracted position, and thus grooves 28 are readily accessible. With shank 21 in this retracted position, a pair of suture tails may be inserted into grooves 28 for subsequent cutting.

When the shank is moved to its suture-holding or intermediate position, prongs 43 are moved to their closed position within grooves 28. The suture tails will then be confined in space 54 which is bounded by prong 43 and the interior wall of groove 28. As shown in FIG. 7, when shank 21 is moved towards the tip of 27, prongs 43 will enter grooves 28, thereby trapping suture tails within grooves 28. Grooves 28 and prongs 43 should be sized such that the suture tails 31 may freely slide within the grooves yet are still held in place by prongs 43. In this manner, after the suture tails are secured within grooves 28 by means of prongs 43, the suture cutting device may be slid along tails 31 towards the knot. Thus, prongs 43 act to prevent the suture tails from escaping from grooves 28 while permitting the suture tails to slide within grooves 28 in a direction substantially perpendicular to the plane of FIG. 7 (i.e., perpendicular to top surface 53 of housing 20).

When shank 21 is further moved to its suture-cutting or extended position, the knife defined by cutting edges 44 is moved to its extended position. As cutting edges 44 are advanced through grooves 28, the cutting edges will cut the suture tails positioned within grooves 28. Since grooves 28 are preferably spaced from distal tip 27, when shank 21 is advanced to its extended position, prongs 43 are advanced into the region of housing 20 located between distal tip 27 and grooves 28 thereby preventing injury to the patient. In this manner, cutting edges 44 are not exposed, thereby eliminating the possibility of injury to the patient or surgeon. FIG. 8 best illustrates the cutting step, wherein shank 21 has been advanced to its cutting position, and has thereby cut a suture tail contained in groove 28.

As mentioned previously, it is generally desired to cut the suture tails a predetermined distance from the knot from which the tails extend. For most surgical procedures, this distance is between about 0.20 and about 0.25. As best shown in FIG. 9, knot 32 is positioned atop surface 53 on neck 26. As will be apparent, therefore, suture tail 31 can be cut at a predetermined distance from knot 32. The length of suture tail remaining after a cutting operation using the device of the present invention can be readily modified by merely adjusting the distance between the plane of the knife and top surface 53 of neck 26. This distance can be adjusted by modifications to the thickness of neck 26, the width of space 29, and the distance between space 29 and shank 21. Thus, various configurations may be employed in order to insure that the proper amount of suture tail is left.

Figure 5:
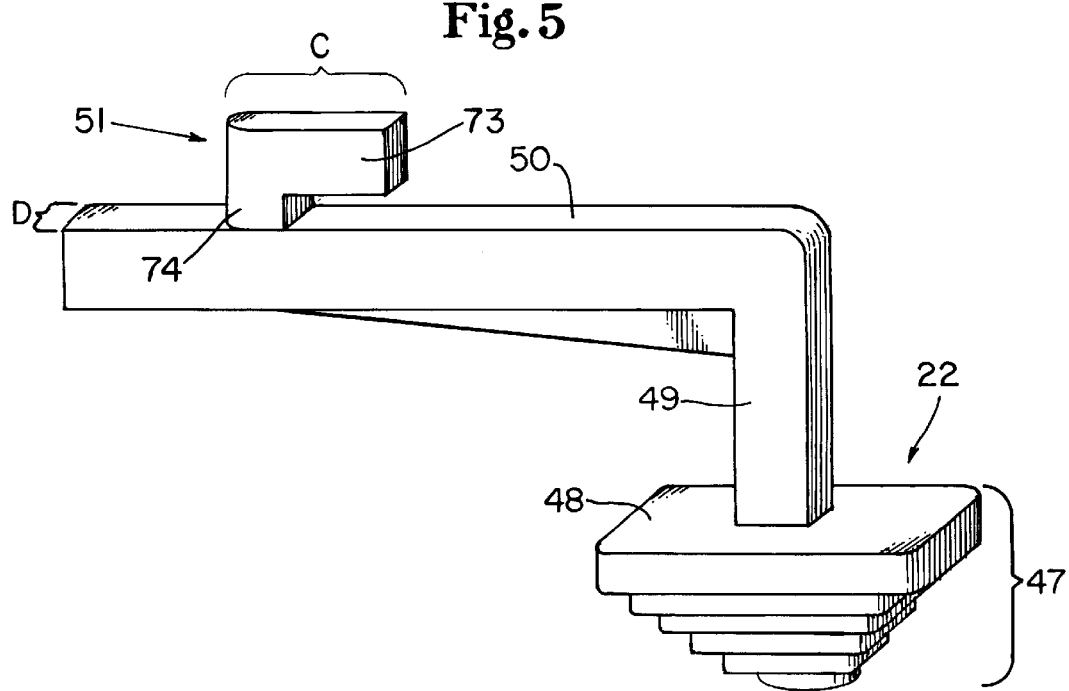
FIG. 5 is a perspective view of the actuator of the suture cutter of the present invention.

Any of a number of means may be employed for moving shank 21, and one preferred embodiment is actuator 22 shown in FIG. 5. Actuator 22 comprises thumb button 47 having a flat bottom surface 48, and an actuator arm 50 which is attached to bottom surface 48 by means of support post 49. Hook 51 is provided adjacent the end of actuator arm 50, and hook 51 is configured to be insertable within slot 45 of shank 21 as will be more fully described below 45.

Slot 45 of shank 21 has a length A and a width B (see FIG. 4). Hook 51 comprises upper arm 73 and lower arm 74 which are arranged at right angles to one another. Lower arm 74 is attached to actuator arm 50. The length C of upper arm 73 is preferably only slightly less than width B of slot 45 on shank 21, and the width D of upper arm 73 is preferably only slightly less than the length A of slot 45. In this fashion, actuator arm 50 may be positioned such that its longitudinal axis is perpendicular to the longitudinal axis of shank 21, thereby permitting upper arm 73 to be inserted into slot 45. After upper arm 73 is inserted into slot 45, actuator arm 50 is rotated 90 degrees so that its longitudinal axis is parallel with that of shank 21, thereby resulting in hook 21 extending through slot 45 in the manner best shown in FIG. 2. Width D of upper arm 73 is preferably the same as the width of lower arm 74, and this width should be less than width B of slot 45 on shank 21. The difference in width will permit hook 51 to move laterally within slot 45 perpendicularly to the longitudinal axis of shank 21, an important feature the significance of which is described below.

As best shown in FIG. 2, since hook 51 of actuator 22 engages slot 45 of shank 21, movement of actuator 22 towards tip 27 will cause shank 21 to also move towards tip 27 as desired. Thus, actuator 22 may be employed to effect movement of shank 21 in the manner previously described. During use, it is important that the movement of shank 21 be controlled as much as possible. For example, after the suture tails have been inserted into grooves 28, shank 21 may be moved to its intermediate or suture-holding position. The tip of the suture cutter may then be then be slid towards the knot which may be located in an orifice of the patient's body. While the tip of the cutter is slid along the suture tails toward the knot, however, it is imperative that the shank remain in its suture-holding position with the prongs blocking the entrance to grooves 28. If shank 21 returns to its retracted position, the sutures will become disengaged from grooves 28. On the other hand, if shank 21 moves to its suture cutting position while the tip is being slid along the suture tails, the suture tails will be cut prematurely.

In order to provide the necessary control over the shank movement, support post 49 of actuator 22 is positioned within substantially Z-shaped (or stepped) slot 30 of top-half 23 of the housing. As best shown in FIG. 6, stepped slot 30 comprises first leg 66, second leg 67 and third leg 68. Support post 49 is slidably positioned in slot 30 such that post 49 may move along each of the three legs of slot 30. When support post 49 is positioned against end wall 69 of first leg 66, shank 21 will be in its retracted position as shown in FIG. 2. As support 49 is advanced along first leg 66 towards second leg 67, shank 21 will be urged towards tip 27. When support post 49 reaches second leg 67, shank 21 will be in its suture holding position as best shown in FIG. 7.

While first leg 66 and third leg 68 extend in a direction substantially parallel to the longitudinal access of housing 20, second leg 67 extends substantially perpendicularly between first leg 66 and third leg 68. Since the width D of hook 51 is less than the width B of slot 45 in the shank, support post 49 may be slid sideways along second leg 67 of Z-shaped slot 30 without displacing shank 21. As support post 49 is slid sideways, hook 51 will in turn slide in the same direction within slot 45 of shank 21. In this manner, as the actuator is slid sideways within the Z-shaped slot, which in turn results in support post 49 sliding sideways within second leg 67, shank 21 will remain in its suture-holding position. The advantage this feature provides is that after the suture tails have been inserted into grooves 28, the surgeon may slide thumb button 47 forward, thereby urging shank 21 to its suture-holding position. When the second end wall 71 of first leg 66 is reached, further advancement of shank 21 will not occur unless and until the actuator is urged sideways (via thumb button 47). This feature provides a simple means for the surgeon to insure that shank 21 remains in its suture-holding position while tip 27 of the suture cutter is advanced towards the knot.

Once the knot is reached and is positioned atop space 29 on neck 26, thumb button 47 may be moved sideways thereby moving support post 49 sideways along second leg 67 (as shown in FIG. 7). Once the sideways movement is completed, thumb button 47 may then be further urged forward, which results in support post 49 moving along third leg 68 towards end wall 70. This results in shank 21 advancing further towards tip 27 resulting in the cutting of the suture tails by cutting edges 44 as shown in FIG. 8. The configuration of actuator 22 and stepped (or substantially Z-shaped) slot 30 provides a simple mechanism by which proper use of the suture cutter of the present invention may be ensured.

To further simplify the movement of actuator 22, thumb button 47 is positioned within recess 34 in top half 24 of housing 20 (as best shown in FIG. 1). Recess 34 has an outline which corresponds to the allowed movement of thumb button 47 (as governed by stepped slot 30), and has a top surface 36 upon which bottom surface 48 of thumb button 47 slides. Thus, thumb button 47 may freely slide within recess 34 in the desired manner. In addition, this results in both recess 34 and stepped slot 30 guiding the proper movement of actuator 22. Of course, only one of recess 34 and stepped slot 30 may be employed, if desired.

The foregoing description of preferred embodiments is by no means exhaustive of the variations in the present invention that are possible, and has thus been presented only for purposes of illustration and description. Obvious modifications and variations will be apparent to those skilled in the art in light of the teachings of the foregoing description. For example, a single or multiple grooves may be provided depending upon the number of suture tails to be cut. Multiple grooves may even be provided along the same side of the housing neck. Obvious variations in the shank, suture retainers and knife will readily accommodate such changes in the number or location of grooves. In addition, the suture retainers and knife need not be provided on a single shank. Thus, it is intended that the present invention be defined by the claims appended hereto.

We claim:

1. An apparatus for cutting a suture, said apparatus comprising:

(a) a housing having a groove therein;

(b) a knife moveable between retracted and extended positions, and positioned within said housing such that said knife passes through said groove as it is moved from said retracted position to said extended position, thereby cutting a suture positioned within said groove; and (c) a suture retainer adapted for being moveable between an open position and a closed position, wherein said retainer being configured to permit a suture to be positioned within said groove when the retainer is at the open position, and said retainer being configured to prevent a suture from escaping from said groove when the retainer is at the closed position.

2. The apparatus of claim 1, wherein said apparatus has a pair of said grooves and a pair of said suture retainers.

3. The apparatus of claim 1, wherein said suture retainer and said knife are provided at the distal end of a moveable shank positioned within said housing.

4. The apparatus of claim 2, wherein said suture retainers and said knife are provided at the distal end of a moveable shank positioned within said housing.

5. The apparatus of claim 3, wherein said shank is moveable between retracted, intermediate and extended positions, such that:
   when said shank is at its retracted position, said knife is at its retracted position and said retainer is at its open position;
   when said shank is at its intermediate position, said retainer is at its closed position; and
   when said shank is at its extended position, said knife is at its extended position.

6. The apparatus of claim 5, further comprising an actuator for effecting movement of said shank.

7. The apparatus of claim 5, wherein said suture retainer comprises a prong at the distal end of said shank, and said groove has an entrance, such that said prong blocks the entrance to the groove when said shank is at its intermediate position, thereby preventing a suture from escaping from the groove while still permitting the suture to slide within said groove.

8. The apparatus of claim 7, wherein said knife is located proximally of said prong such that said knife will only enter said groove to cut a suture when the shank is moved from its intermediate position to its extended position.

9. The apparatus of claim 8, wherein said housing has a handle portion and an elongate neck portion, wherein said actuator is located on said handle and said groove is located on said neck.

10. An apparatus for cutting a pair of suture tails, said apparatus comprising:
   (a) a housing having a pair of grooves therein; and
   (b) a knife moveable between retracted and extended positions, and positioned within said housing such that said knife passes through said grooves as it is moved from said retracted position to said extended position, thereby cutting a suture tail positioned within each of said grooves.

11. The apparatus of claim 10, wherein said knife is provided at the distal end of a moveable shank positioned within said housing.

12. The apparatus of claim 11, further comprising at least one suture retainer for preventing suture tails from escaping from said grooves.

13. The apparatus of claim 12, further comprising a pair of said suture retainers, wherein each of said suture retainers comprises a prong extending from the distal end of said shank, and wherein said knife is located proximally of said prongs.

14. The apparatus of claim 13, wherein said shank is moveable between retracted, intermediate and extended positions, such that:
   when said shank is at its retracted position, said knife is at its retracted position and a pair of suture tails may be positioned within said grooves;
   when said shank is at its intermediate position, said prongs prevent the suture tails from escaping from said grooves while still permitting the suture tails to slide within said grooves, thereby permitting said apparatus to be slid along said suture tails to the desired cutting location; and
   when said shank is moved to its extended position, said knife is moved toward its extended position, thereby cutting the suture tails.

15. The apparatus of claim 14, wherein said knife comprises a pair of cutting edges such that when said shank is moved to its extended position, one of said cutting edges passes through each of said grooves.

16. The apparatus of claim 15, wherein said cutting edges are arranged in a V-shaped configuration.

17. The apparatus of claim 14, further comprising an actuator for effecting movement of said shank.

18. The apparatus of claim 17, wherein said housing has a handle portion and an elongate neck portion, wherein said actuator is located on said handle and said grooves are located on said neck.

19. The apparatus of claim 18, wherein said actuator is moveable in a substantially Z-shaped pattern corresponding to the retracted, intermediate and extended positions of said shank.

20. A method for cutting a pair of suture tails extending from a knot, said method comprising the steps of:
   (a) providing a suture cutter, said cutter comprising:
      a housing having a pair of grooves therein; and
      a knife moveable between retracted and extended positions, and positioned within said housing such that said knife will cut a suture tail positioned within each of said grooves as the knife is moved to its extended position;
   (b) positioning one of said tails in each of said grooves while said knife is at its retracted position; and
   (c) moving said knife through said pair of grooves to its extended position, thereby cutting said suture tails adjacent said knot.

21. The method of claim 20, further comprising the step of sliding said suture cutter along said suture tails to said knot prior to cutting said tails, thereby cutting said tails at a predetermined distance from said knot.

22. The method of claim 21, wherein said suture cutter further comprises a pair of suture retainers for preventing said suture tails from escaping from said grooves while still permitting the suture cutter to slid along said suture tails.

23. The method of claim 22, wherein said suture retainers are moveable between open and closed positions, such that said retainers permit the suture tails to be positioned within said grooves when in the open position and said retainers prevent the suture tails from escaping from said grooves when in the closed position, and further comprising the step of moving said suture retainers to their closed position after the step of positioning one of said tails in each of said grooves.

24. The method of claim 22, wherein said housing comprises a handle portion and an elongate neck portion, with said grooves positioned on opposite sides of said neck.

25. The method of claim 24, wherein said suture retainers and said knife are provided at the distal end of a moveable shank positioned within said housing, said shank moveable between retracted, intermediate and extended positions, and wherein:
   said shank is in its retracted position when said suture tails are positioned within said grooves while said knife is at its retracted position;
   said suture retainers are moved to their closed position by moving said shank to its intermediate position; and
   said knife is moved to its extended position by moving said shank to its extended position.

26. The method of claim 25, wherein said suture cutter further comprises an actuator for moving said shank.

27. An apparatus for cutting a suture, said apparatus comprising:
   (a) a housing having a groove therein; and
   (b) a shank moveable among a open position, a closed position, and an extended position, and positioned within said housing such that said shank being configured to permit a suture to be positioned within said groove when said shank is at said open position, said shank being configured to prevent a suture from escaping from said groove when said shank is at said closed position, and said shank being configured to cut a suture positioned within said groove when advanced from said closed position to said extended position.

28. The apparatus of claim 27, wherein said shank comprises a suture retainer and a knife, said suture retainer and said knife being provided at the distal end of said shank.

29. The apparatus of claim 28, wherein said suture retainer comprises a prong at the distal end of said shank, and said groove has an entrance, such that said prong blocks the entrance to the groove when said shank is at its closed position, thereby preventing a suture from escaping from said groove while still permitting the suture to slide within said groove.

30. The apparatus of claim 29, wherein said knife is located proximally of said prong such that said knife will only enter said groove to cut a suture when said shank is moved from said closed position to said extended position.

31. The apparatus of claim 27, further comprising an actuator for effecting movement of said shank.

32. The apparatus of claim 31, wherein said housing has a handle and an elongate neck, wherein said actuator is located on said handle and said groove is located on said neck.

* * * * *